United States Patent
Kung et al.

(10) Patent No.: US 8,481,766 B2
(45) Date of Patent: Jul. 9, 2013

(54) METHODS OF PRODUCING EPOXIDES FROM ALKENES USING A TWO-COMPONENT CATALYST SYSTEM

(75) Inventors: Mayfair C. Kung, Wilmette, IL (US); Harold H. Kung, Wilmette, IL (US); Jian Jiang, Shanghai (CN)

(73) Assignee: Northwestern University, Evanston, IL (US)

( * ) Notice: Subject to any disclaimer, the term of this patent is extended or adjusted under 35 U.S.C. 154(b) by 418 days.

(21) Appl. No.: 12/943,138

(22) Filed: Nov. 10, 2010

(65) Prior Publication Data

US 2011/0112315 A1 May 12, 2011

Related U.S. Application Data

(60) Provisional application No. 61/259,828, filed on Nov. 10, 2009.

(51) Int. Cl.
*C07D 301/06* (2006.01)

(52) U.S. Cl.
USPC .......................................................... 549/533

(58) Field of Classification Search
USPC .......................................................... 549/533
See application file for complete search history.

(56) References Cited

PUBLICATIONS

Nijhuis et al., The Production of Propene Oxide: Catalytic Processes and Recent Developments, Industrial & Engineering Chemistry Research, Apr. 4, 2006, pp. 3447-3459, vol. 45, No. 10, American Chemical Society.

Nijhuis et al., Direct Epoxidation of Propene Using Gold Dispersed on TS-1 and Other Titanium-Containing Supports, Industrial & Engineering Chemistry Research, Feb. 4, 1999, pp. 884-891, vol. 38, No. 3, American Chemical Society.

Jiang et al., Aqueous phase epoxidation of 1-butene catalyzed by suspension of $Au/TiO_2$ + TS-1, Gold Bulletin, 2009, vol. 42, No. 4.

Nijhuis et al., Processes and Possibilities for the Epoxidation of Propene, Prepr. Pap.-Am. Chem. Soc., Div. Pet., 2006, vol. 51, Nos. 1 & 2.

Sinha et al., Catalysis by gold nanoparticles: epoxidation of propene, Topics in Catalysis, Jun. 2004, pp. 95-102, vol. 29, Nos. 3-4.

*Primary Examiner* — Bernard Dentz
(74) *Attorney, Agent, or Firm* — Bell & Manning, LLC

(57) ABSTRACT

Methods for the epoxidation of alkenes are provided. The methods include the steps of exposing the alkene to a two-component catalyst system in an aqueous solution in the presence of carbon monoxide and molecular oxygen under conditions in which the alkene is epoxidized. The two-component catalyst system comprises a first catalyst that generates peroxides or peroxy intermediates during oxidation of CO with molecular oxygen and a second catalyst that catalyzes the epoxidation of the alkene using the peroxides or peroxy intermediates. A catalyst system composed of particles of suspended gold and titanium silicalite is one example of a suitable two-component catalyst system.

15 Claims, 10 Drawing Sheets

Scheme 1

Scheme 2

METHODS OF PRODUCING EPOXIDES FROM ALKENES USING A TWO-COMPONENT CATALYST SYSTEM

CROSS-REFERENCE TO RELATED APPLICATIONS

This applications claims priority from U.S. provisional patent application Ser. No. 61/259,828, filed on Nov. 10, 2009, the entire disclosure of which is incorporated herein by reference.

STATEMENT REGARDING FEDERALLY SPONSORED RESEARCH OR DEVELOPMENT

This invention was made with government support under DE-FG02-01ER15184 awarded by Department of Energy. The government has certain rights in the invention.

BACKGROUND OF THE INVENTION

Epoxides are important intermediates for chemicals synthesis. They are precursors to large volume commodity chemicals such as ethylene glycol and propylene glycol that can be used as solvents, polymers such as polypropylene oxide, and many enantiomeric molecules that are intermediates for pharmaceutical and natural products synthesis. They are produced by selective oxidation of the corresponding alkenes via insertion of an oxygen atom across the carbon-carbon double bond. The common oxygen sources are peroxides, hydroperoxides, oxychlorides, and oxometal complexes. While effective, these reagents are expensive and their use is not environmentally friendly, generating significant amounts of unwanted byproducts. A much more desirable oxidant is molecular oxygen. To date, however, success in epoxidation with molecular oxygen is limited to activated terminal alkenes or alkenes without allylic hydrogens, such as ethylene and butadiene. (See R. B. Grant, and R. M. Lambert, Mechanism of the silver-catalyzed heterogeneous epoxidation of ethylene, *Journal of the Chemical Society*, Chemical Communications (1983) 662-3 and J. W. Medlin, J. R. Monnier, and M. A. Barteau, Deuterium Kinetic Isotope Effects in Butadiene Epoxidation over Unpromoted and Cs-Promoted Silver Catalysts, *Journal of Catalysis* 204 (2001) 71-76). Epoxidation of, for example, propene, could be achieved with reasonable yields only by using oxidants such as nitrous oxide or hydrogen peroxide. (See E. Ananieva and A. Reitzmann, Direct gas-phase epoxidation of propene with nitrous oxide over modified silica supported $FeO_x$ catalysts, *Chemical Engineering Science* 59 (2004) 5509-5517; T. Thoemmes, S. Zuercher, A. Wix, A. Reitzmann, and B. Kraushaar-Czarnetzki, Catalytic vapour phase epoxidation of propene with nitrous oxide as an oxidant, *Applied Catalysis, A: General* 318 (2007) 160-169; and L. Y. Chen, G. K. Chuah, and S. Jaenicke, Propylene epoxidation with hydrogen peroxide catalyzed by molecular sieves containing framework titanium, *Journal of Molecular Catalysis A: Chemical* 132 (1998) 281-292.)

There has been limited success in the epoxidation of unactivated alkenes with molecular oxygen because it is such a demanding reaction. Known commercial processes are the Ag catalyzed epoxidation of ethylene and butadiene. (See R. B. Grant and R. M Lambert, *J. Chem. Soc., Chem. Commun.*, 1983, 662 and J. Will Medlin, John R. Monnier and Mark A. Barteau, *J. Catal.*, (2001) 204, 71). These catalytic processes however fail when the alkene possesses allylic hydrogen.

Recently, there has been extensive exploration using supported Au catalyst for alkene epoxidation with molecular $O_2$. These studies fall into three classes, those with molecular $O_2$ alone, those with the addition of peroxy initiator, and those that require a sacrificial reductant. Very low yields of propene epoxidation were observed using $H_2O$, $O_2$, and $C_3H_6$ over $Au/TiO_2$ catalysts. Turner et. al. reported epoxidation of styrene to benzaldehyde, styrene epoxide and acetopheneone over $Au_{55}$ clusters. (See M. Ojeda and E. Iglesia, *Chem. Commun.* (Cambridge, U. K.), 2009, 352 and M. Turner, V. B. Golovko, O. P. H. Vaughan, P. Abdulkin, A. Berenguer-Murcia, M. S. Tikhov, B. F. G. Johnson and R. M. Lambert, *Nature* (London, U. K.), 2008, 454, 981). However, the activity and the selectivity for epoxide were low. The addition of a peroxy initiator accelerated the epoxidation reaction, but the product distribution appeared to be very solvent dependent. (See M. D. Hughes, Y.-J. Xu, P. Jenkins, P. McMorn, P. Landon, D. I. Enache, A. F. Carley, G. A. Attard, G. J. Hutchings, F. King, E. H. Stitt, P. Johnston, K. Griffin and C. J. Kiely, *Nature* (London, U. K.), 2005, 437, 1132). Perhaps the most intensely studied system is one in which $H_2$ was included as a sacrificial reductant, and the catalysts used were $Au/TiO_2$, Au/TS-1 and Au/MCM-41 and Au—Ba/Ti-TUD. (See E. E. Stangland, K. B. Stavens, R. P. Andres and W. N. Delgass, *J. Catal.*, 2000, 191, 332; A. K. Sinha, S. Seelan, S. Tsubota, and M. Haruta, *Topics in Catalysis*, 2004, 29, 95; and J. J. Bravo-Suarez, K. K. Bando, J. Lu, M. Haruta, T. Fujitani and S. T. Oyama, *J. Phys. Chem. C*, 2008, 112, 1115). The proposed mechanism for these catalysts involves the formation of $H_2O_2$ on the Au active site and the migration of the peroxide onto neighboring Ti to form Ti hydroperoxy species which can donate an [O] atom to propylene to form propylene epoxide. (See J. J. Bravo-Suarez, K. K. Bando, J. Lu, M. Haruta, T. Fujitani and S. T. Oyama, *J. Phys. Chem. C*, 2008, 112, 1115).

A recent report by Ketchie et. al. suggested an alternate route to generate $H_2O_2$ without using $H_2$ (See Ketchie, W. C., Murayama, M., and Davis, R. J., *Topics in Catalysis*, 44 (1-2), 307 (2007). They found that during the Au-catalyzed CO oxidation in water at ambient temperature, $H_2O_2$ was formed in the aqueous phase.

BRIEF SUMMARY

Methods for the epoxidation of alkenes are provided. The methods include the steps of exposing the alkene to a two-component catalyst system in an aqueous solution, in the presence of carbon monoxide and molecular oxygen, under conditions in which the alkene is epoxidized. The two-component catalyst system comprises a first catalyst that generates peroxides or peroxy intermediates during oxidation of CO with molecular oxygen and a second catalyst that catalyzes the epoxidation of the alkene using the peroxides or peroxy intermediates. A catalyst system composed of particles of suspended gold and titanium silicalite is one example of a suitable two-component catalyst system.

The methods can be conducted at low temperatures and can be used to produce epoxides very selectively. In some embodiments the epoxidation is carried out at a temperature of no greater than about 50° C. (e.g., no greater than about 40° C.). In some embodiments the epoxide is produced with at least 80% selectively. This includes embodiments in which the epoxide is produced with at least 90% selectively and further includes embodiments in which the epoxide is produced with at least 99% selectively.

The aqueous solvent system is desirably a mixture of water and an alcohol, such as methanol or ethanol. The ratio of alcohol to water in the mixture is desirably at least 4:1 by volume. For example, the ratio can be from about 4:1 to about 40:1.

The methods are particularly well-suited for the epoxidation of alkenes having at least one allylic hydrogen, such as butene or propene. The methods can be carried out in the absence of $H_2$ gas and peroxy initiators.

DETAILED DESCRIPTION

Figure 1:
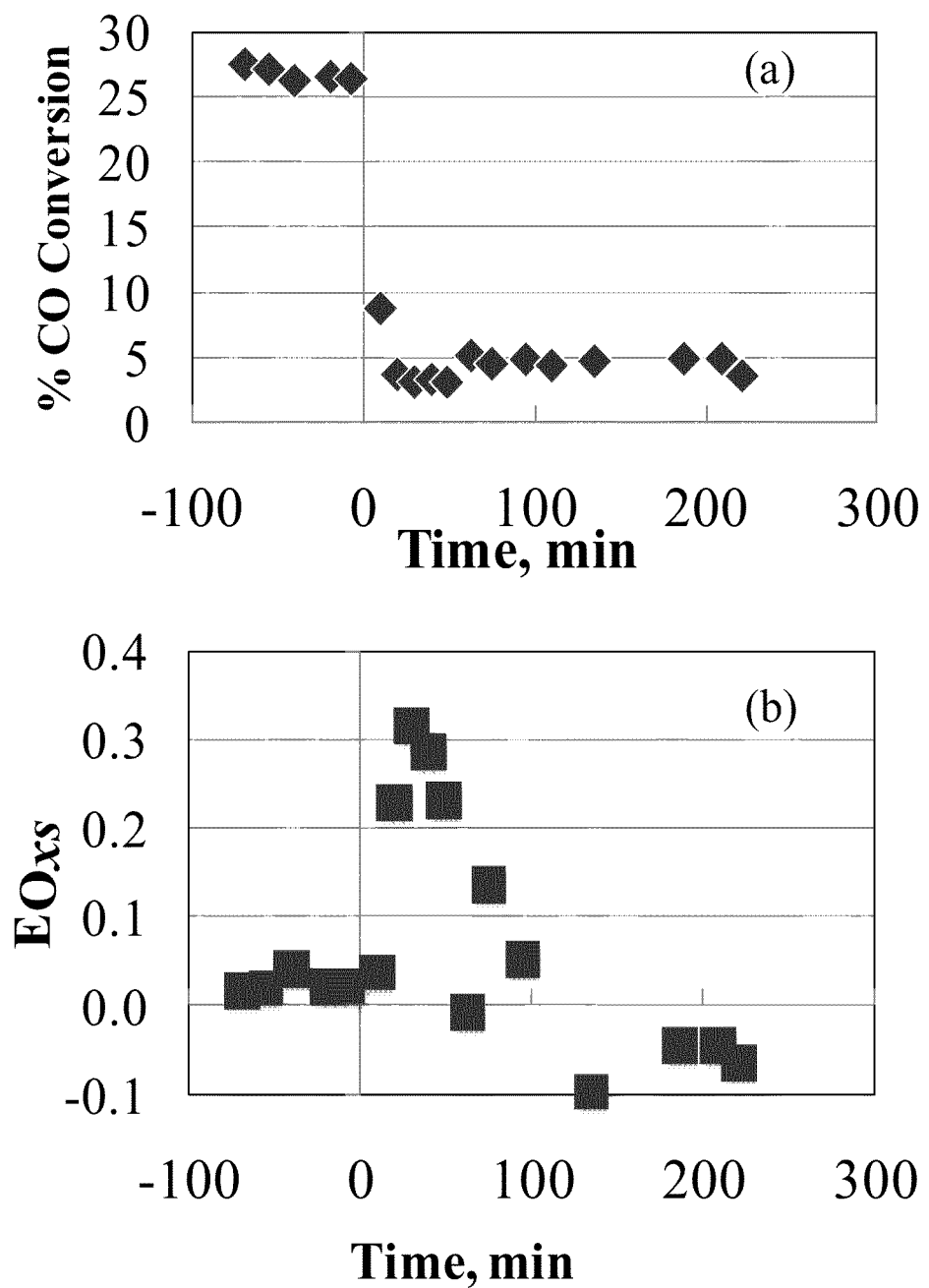
FIG. 1 shows (a) % CO conversion and (b) efficiency of $EO_{xs}$ as a function of time for Example 1. Reaction condition: 2.5% CO, 1.25% $O_2$ and balance He over $Au/TiO_2$ catalyst at 25° C.

One aspect of the invention provides a method for the epoxidation of unsaturated hydrocarbons, particularly hydrocarbons having at least one allylic hydrogen. In one embodiment of the present methods, highly selective epoxidation of alkenes, including propene and butene, can be achieved using molecular oxygen in water, or in a dilute solution of water in an alcohol, catalyzed by a suspension of a two-component catalyst system. The methods can be carried out in the absence of $H_2$ and in the absence of peroxy initiators. In these methods, CO is consumed as a sacrificial reductant, but can be regenerated from the byproduct $CO_2$ using known processes such as reverse water-gas shift, resulting in an overall environmentally very friendly and easily scalable process. As such, the present methods can provide an environmentally friendly method to generate alkyl peroxides in situ that can be used to synthesize organic epoxides, replacing the use of expensive and environmentally unfriendly organic hydroperoxides. In a solvent comprising a mixture of water and methanol, selective (~100% selective) production of epoxide can be achieved.

The two-component catalyst system includes a first catalyst that generates peroxides, such as hydrogen peroxide or alkyl peroxides, or peroxy intermediates during oxidation of CO with molecular oxygen in the presence of an aqueous solvent or alcohol-water mixture and a second catalyst that catalyzes the epoxidation of alkenes using the peroxides or peroxy intermediates. For example, one catalyst system is a mixture of $Au/TiO_2$ (i.e., particles of gold supported on titanium dioxide) and titanium silicalite (TS-1). In this system, the $Au/TiO_2$, having low temperature CO oxidation activity, would generate $H_2O_2$ or ROOH, which would be used by the TS-1 for epoxidation. The two catalyst components can be present in two separate phases (as shown by the examples, below), or as a composite.

Other than titanium silicalite, other catalysts active in catalyzing epoxidation of alkenes using peroxides can be used. This includes vanadium substituted silicalite, manganese substituted zeolites, titanium substituted silsequioxane, oxorhenium complexes, and the like, provided that they are stable under the reaction conditions and not highly active in decomposing peroxides. Other supports for the metal (e.g., Au) catalyst also can be used, including carbon, magnesium oxide, aluminum oxide, cerium oxide, or mixed oxides such as titanium-silica oxide. The oxide support should be selected such that it is not active in decomposing hydrogen peroxide or organic peroxide, catalyzing hydrolysis of or isomerization of epoxides, polymerization of epoxides, or any undesirable reactions of epoxides including oxidation or solvolysis.

Conducting the epoxidation in an alcohol-water mixture, such as a methanol-water mixture is preferable to carrying out the epoxidation in water, which results in the production of a substantial fraction of glycol, rather than epoxide, due to hydrolysis of the epoxide. The use of an alcohol-water solvent mixture is also preferable to an anhydrous methanol solvent, which fails to produce epoxide.

In addition to methanol, other alcohols that are miscible with water can be used in the solvent mixture. Optionally, other organic solvents that are miscible with water and alcohol also can be present in the solvent mixture, such as tetrahydrofuran, dichloromethane, dimethylsulfoxide, acetone, ethers, and ketones. Such solvents can assist in enhancing the solubility of the reactants.

The following examples illustrate embodiments of the present methods for the epoxidation of butene and propene.

EXAMPLES

Example 1

In this example, a combination of two catalysts, $Au/TiO_2$ and TS-1 were used to catalyze the demanding reaction of butene epoxidation in an aqueous solution using molecular oxygen under very mild reaction conditions. Peroxy initiator was not necessary but carbon monoxide as a sacrificial reductant was used.

Methods

The two different batches of $Au/TiO_2$ catalysts used in the reaction (denoted $Au/TiO_2$-02-4 and $Au/TiO_2$-02-9) were supplied by the World Gold Council. There was no observable difference in their catalytic performance. The Au loadings of $Au/TiO_2$-02-4 and $Au/TiO_2$-02-9 were 1.51 and 1.49 wt. % and the average Au particle sizes were 3.8±1.5 nm and 3.6±1.32 nm, respectively. TS-1 was synthesized using the method of Thangaraj et al. (See A. Thangaraj, R. Kumar, S. P. Mirajkar and P. Ratnasamy, *J. of Catal.*, 1991, 130, 1). Diffuse reflectance UV visible spectroscopy (Perkin Elmer LAMBDA 1050) was used to verify the absence of extra framework Ti. The silicalite sample was synthesized using the same procedure as for TS-1, except that TiBuOH was omitted.

The epoxidation reaction was carried out in a high pressure glass reactor (Cole-Parmer) which contained 50 mL of ion-exchanged distilled water (DDI $H_2O$, pH~5.5). The reactor was maintained at 40° C. (except when specified). The gas feed composition, 2.5% CO, 1.25% $O_2$ and 1.25% 1-butene, balance He, was adjusted using 5850E Brooks flow controllers. 40 mL min$^{-1}$ of the feed gas was directed into the aqueous phase through a 5 μm stainless steel porous frit (Scientific Instrument Services). The pressure in the vessel was maintained at 480 kPa with a back pressure regulator (Mighty Mite). The experiments were started with the catalysts (0.1 g $Au/TiO_2$±0.15 g TS-1) placed above the liquid level in a small polyethylene cup with a small magnet in the cup and held in place by a rare earth magnet placed outside the reactor. At a predetermined time (defined as time=0), the rare earth magnet was used to guide the cup into the water, thereby initiating the aqueous phase catalytic reaction. After the reaction, 50 mL of $H_2O$ was used to replace the $H_2O$-catalysts mixture and the feed was again introduced at 480 kPa to calibrate the gas chromatography (GC) areas of the different components of the feed. The exit gas from the reactor was monitored with on-line GC. All liquid products were separated from the solid catalysts by filtration through a 0.2 μm polyvinylidene fluoride (PVDF) membrane (Pall) and analyzed with an Agilent 6890 GC.

Due to the high solubility of $CO_2$ in water, it was difficult to obtain good instantaneous carbon balance to assess the importance of the combustion pathway. This value can however be assessed by summing $O_{xs}$ (defined as that O beyond what is required for stoichiometric CO oxidation) over time and comparing it with the total alkene reacted or epoxide formed. $O_{xs}$ can be calculated from $R_{Oxs}$ which is the difference in the rates of oxygen atom and CO consumption (Eq. 1). The efficiency of generation of $O_{xs}$ from CO oxidation is defined in Eq. 2.

$$R_{Oxs} = 2*R_{O2\,used} - R_{CO\,used} \quad (1)$$

$$E_{Oxs} = R_{Oxs}/R_{CO} = \text{efficiency in } O_{xs} \text{ production} \quad (2)$$

Results $Au/TiO_2$

FIG. 1a shows CO oxidation over a $Au/TiO_2$ catalyst at room temperature in a feed of 2.5% CO and 1.25% $O_2$ in He. Before t=0, the catalyst was suspended above the liquid in a small polyethylene cup. It was relatively active for CO oxidation, albeit due to diffusion limitation, the activity was noticeably lower than when the same catalyst was placed in a plug flow reactor. At t=0, the catalyst was dispersed into the aqueous phase and the CO conversion decreased sharply due to the low solubility of the gases in $H_2O$. $E_{Oxs}$ was zero in the gas phase but increased transiently to a value of ~0.3 before decaying to zero after around 100 min (FIG. 1b). When the experiment was repeated with half the amount of catalyst, the aqueous phase CO conversions and $E_{Oxs}$ did not change significantly suggesting that the rate limiting factor was not the catalytic process but the dissolution of gases into the liquid. At the end of the experiment, with 0.05 g $Au/TiO_2$ catalyst, there were 5.2 μmoles of $H_2O_2$ in the aqueous phase. The amount of $H_2O_2$ detected exceeded the amount expected from the equilibrium concentration of the oxidation of $H_2O$ with $O_2$ by many orders of magnitude ($K_{25}=2.58*10^{-22}$ for $H_2O$ oxidation with $O_2$).

Figure 2:
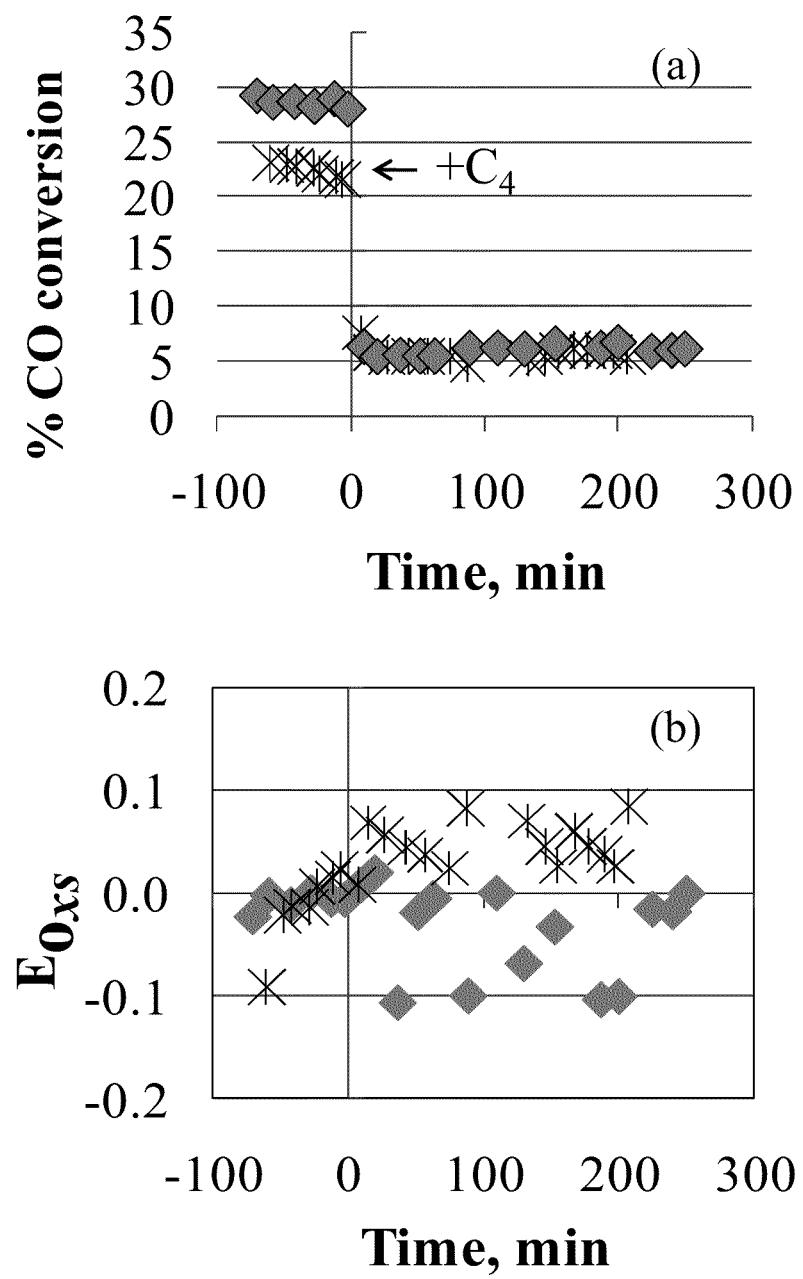
FIG. 2 shows (a) % CO conversions and (b) EOxs over $Au/TiO_2$ catalyst at 40° C. for Example 1. ◇: feed contains 2.5% CO and 1.25% $O_2$ in He; ж: feed contains 2.5% CO, 1.25% $O_2$ and 1.25% $C_4H_8$ in He.

FIG. 2a shows that when the $H_2O$ temperature was increased to 40° C., CO conversions in the gas phase (gas phase temperature was less than 40° C.) and aqueous phase increased slightly. When 1.25% 1-butene was included in the feed, CO conversion was slightly suppressed in the gas phase but remained unaffected in the aqueous phase. The $E_{Oxs}$ was close to zero, with and without butene in the feed, and was much less than that observed at the room temperature reaction condition (FIG. 2b). Thus, no epoxide was formed without the second component of this binary catalyst system.

$Au/TiO_2$+TS-1 Mixture

Figure 3:
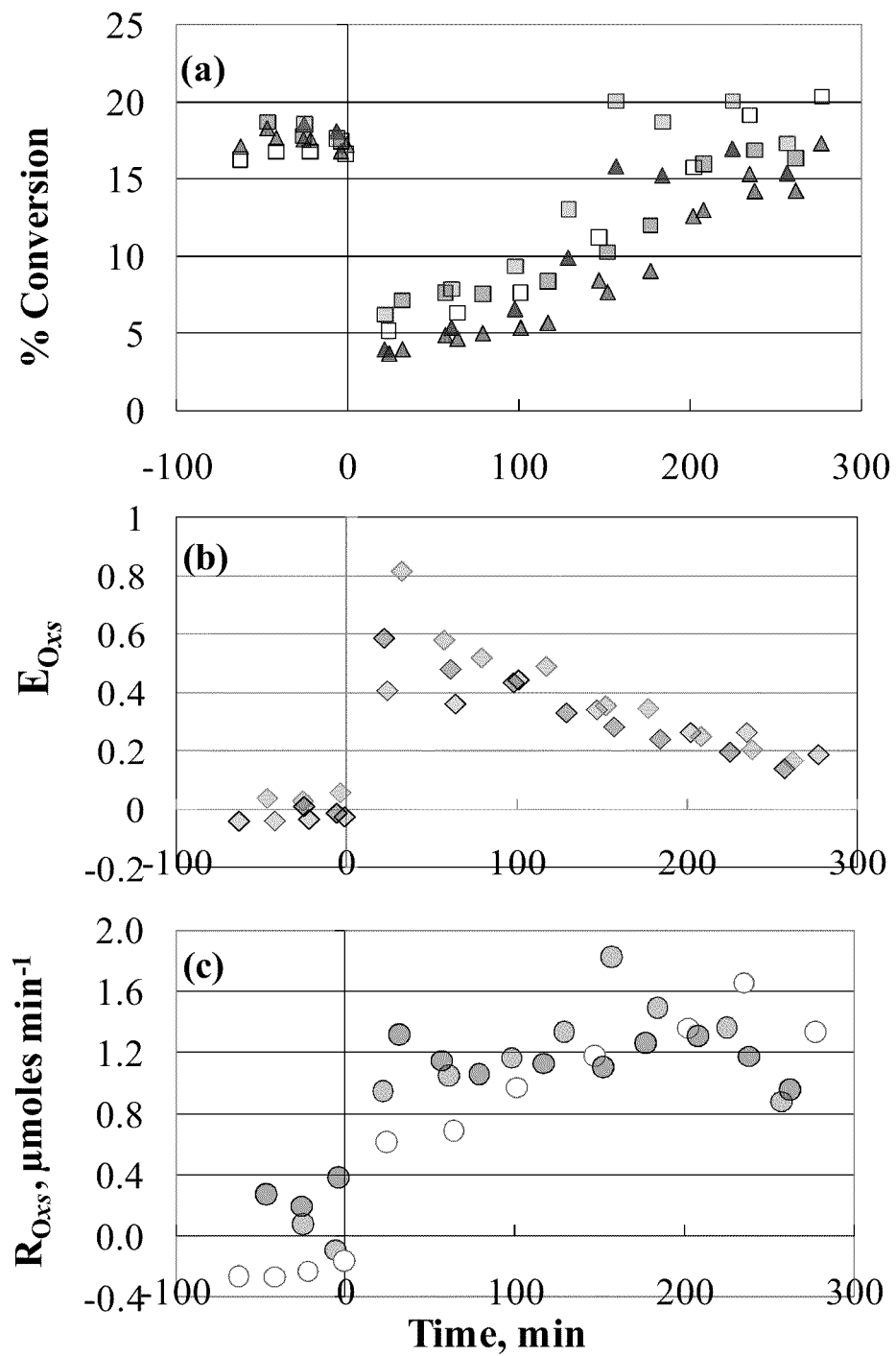
FIG. 3 shows (a) % CO and $O_2$ conversions, (b) $E_{Oxs}$ and (c) $R_{Oxs}$ over $Au/TiO_2$+TS-1 binary catalytic system at 40° C. for Example 1. □: $O_2$ conversion, Δ: CO conversion; ◇: $E_{Oxs}$, O: $R_{Oxs}$. Each shaded set for 3(a), (b) and (c) corresponds to the same run.

FIG. 3a shows the CO and $O_2$ conversions for three separate runs in a feed of CO, $O_2$ and 1-butene using the binary catalyst system of $Au/TiO_2$+TS-1. Table 1 summarizes these results as well as results of control experiments. CO conversion in the gas phase was lower than the runs without TS-1 because diffusional effects were more severe in a deeper bed in the polyethylene cup due to the presence of TS-1. In the gas phase, within uncertainties, the $O_2$ and CO conversions followed the stoichiometric ratio for CO oxidation. Once the catalysts were dispersed into the aqueous phase, $O_2$ conversions were consistently higher than the stoichiometric amounts for the corresponding CO conversions. Both CO and $O_2$ conversions increased with time on stream until at the end of the experiment their conversions were similar or higher than that of the initial gas phase conversions, whereas the rate of $O_{xs}$ production remained constant and positive (FIG. 3c).

Figure 4:
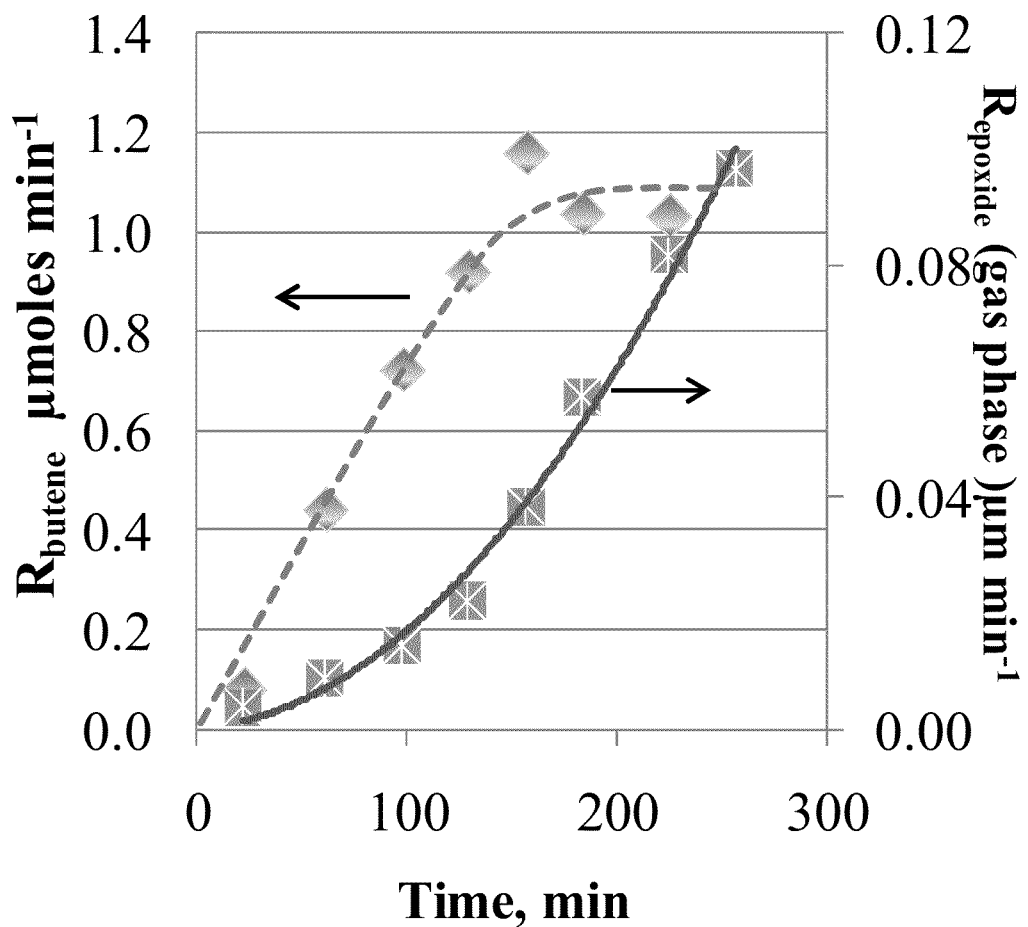
FIG. 4 shows the rates of butene consumption and butene 1,2-epoxide formation as observed in the gas phase in Example 1.
Figure 5:
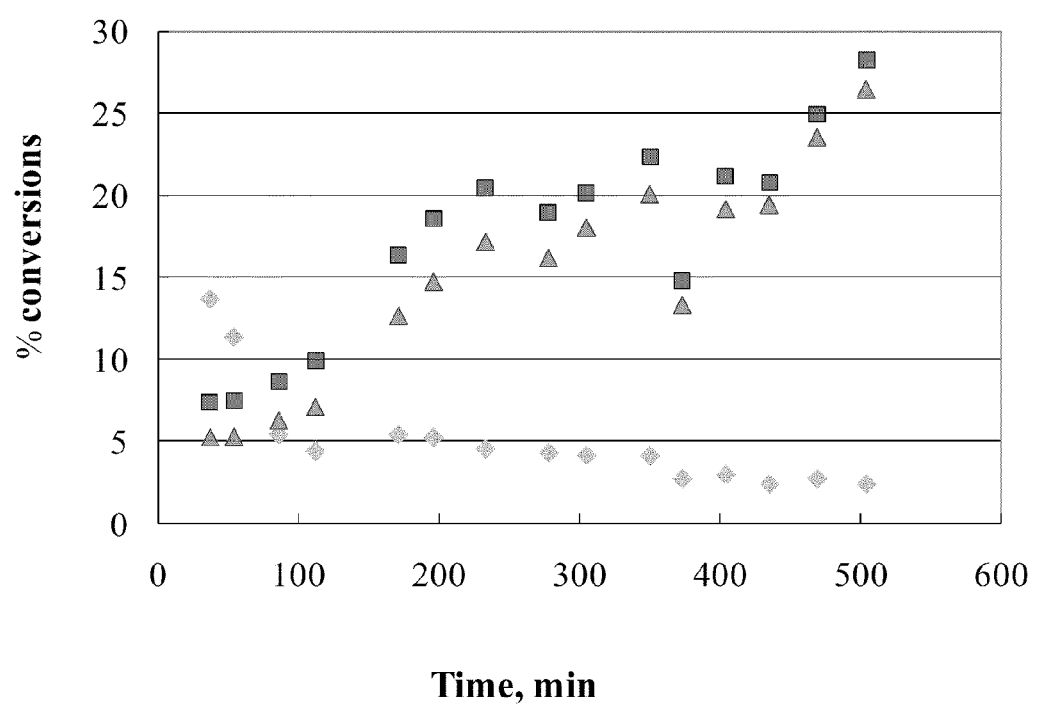
FIG. 5 shows conversions as a function of time on stream over $Au/TiO_2$+TS-1 in the aqueous phase at 40° C. for Example 1. □ $O_2$, Δ CO, ◇ 1-butene.

Upon dispersing the catalysts into $H_2O$ (t=0), butene 1,2-epoxide was detected in the gas phase. The epoxide amount detected in the gas phase was low initially, as most of it was dissolved in $H_2O$, but grew with time as its concentration in solution increased (FIG. 4). Gas phase butene consumption was low initially as dissolved butene was utilized first ($5.62*10^{-5}$ moles was dissolved in 50 mL $H_2O$ as calculated from E. Wilhelm, R. Battino, and R. Wilcock, *Chem. Rev.*, 1977, 77, 219) and the steady state was only reached after 150 min. In a separate extended time experiment (FIG. 5), in which the catalysts were placed in $H_2O$ right at the beginning (thus, the data before 80 min are not steady state data), it was observed that even after 500 min, CO and $O_2$ conversions appeared to be continually increasing, while butene conversion appeared to be steady for a while before it declined slightly with long time on stream. The increases in CO and $O_2$ conversions were only observed in the binary catalytic system of $Au/TiO_2$ and TS-1 and were not observed if $Au/TiO_2$ was used without TS-1 or a mixture of $Au/TiO_2$ and silicalite was used (silicalite has the same crystal structure as TS-1 but without Ti incorporation), or when butene was omitted from the feed.

These results confirmed the formation of butene 1,2-epoxide by direct detection in the exit gas and in the product solution. Table 1 shows that in addition to epoxides, 1,2-butane diol was detected in the product solution as the major oxygenated hydrocarbon product, which was formed by rapid hydrolysis of the epoxide in an aqueous medium. The results also showed that combustion of butene was insignificant under these conditions because, within experimental uncertainties: (1) The sum of moles of hydrogen peroxide, epoxide and diol was close to that of the total moles of $O_{xs}$, whereas the total combustion of one mole of butene to $CO_2$ and $H_2O$ would require 12 moles of $O_{xs}$, and (2) The alkene consumed integrated over time was close to the sum of epoxide and diol integrated over the same time period.

The results of control experiments, runs 4 to 7 in Table 1, showed that all components are needed for epoxide formation, which include CO, $O_2$, supported Au catalyst for peroxide generation, butene, and TS-1 for epoxidation.

TABLE 1

Experimental results for butene epoxidation using Au/TiO$_2$ and TS-1 in an aqueous solution. Reaction conditions: 40° C., feed 2.5% CO, 1.25% O$_2$, 1.25% 1-butene.

| | | | Quantity, ×10$^{-5}$ moles$^3$ | | | | |
|---|---|---|---|---|---|---|---|
| Run # | Catalyst | Feed | Total Epoxide (gas/liquid) | Diol | $O_{xs}$ | Butene consumed | $H_2O_2$ |
| 1 | Au/TiO$_2$ + TS-1 | CO + O$_2$ + C$_4$H$_8$ | 3.0 (0.8/2.2) | 15 | 31 | 19 | 0.4 |
| 2 | Au/TiO$_2$ + TS-1 | CO + O$_2$ + C$_4$H$_8$ | 2.0 (0.6/1.4) | 14 | 30 | 29 | 0.3 |
| 3 | Au/TiO$_2$ + TS-1 | CO + O$_2$ + C$_4$H$_8$ | 3.6 (0.7/2.9) | 18 | 30 | 26 | 0.6 |
| 4 | Au/TiO$_2$ + TS-1 | O$_2$ + C$_4$H$_8$ | 0 | 0 | 0 | 0 | 0 |
| 5 | Au/TiO$_2$ + TS-1 | CO + O$_2$ | ND$^a$ | ND | ~6 | ND | ND |
| 6 | TS-1 | CO$_2$ + O$_2$ + C$_4$H$_8$ | 0 | 0 | 0 | 0 | 0 |
| 7 | Au/TiO$_2$ + silicalite | CO$_2$ + O$_2$ + C$_4$H$_8$ | trace | 0 | 0 | not detectable | 0.6 |

$^a$ND = Not Determined

Example 2

This example illustrates the carbon monoxide-assisted epoxidation of propene using molecular oxygen and a catalyst system of Au/TiO$_2$ and TS-1.

Methods

Materials:

Au/TiO$_2$ catalysts were supplied by the World Gold Council. Two different batches labeled Au—TiO$_2$-02-4 and Au—TiO$_2$-02-9 were used. The Au loadings were 1.51 and 1.49 wt. % and the average Au diameters were 3.8±1.5 nm and 3.6±1.32 nm, respectively. There was no discernible difference in the catalytic performances of the two catalysts. TS-1 was synthesized using the method of Thangaraj et al. (See Thangaraj, A., Kumar, R., Mirajkar, S. P., and Ratnasamy, P., *Journal of Catalysis* 130 (1), 1 (1991)). The incorporation of Ti into the silicalite framework was verified using diffuse reflectance UV visible spectroscopy (Perkin Elmer LAMBDA 1050). The Ti content was 1.0 wt. %, as determined by ICP. The silicalite sample was synthesized using the same procedure as for TS-1, except that no TiBuOH was added.

Figure 6:
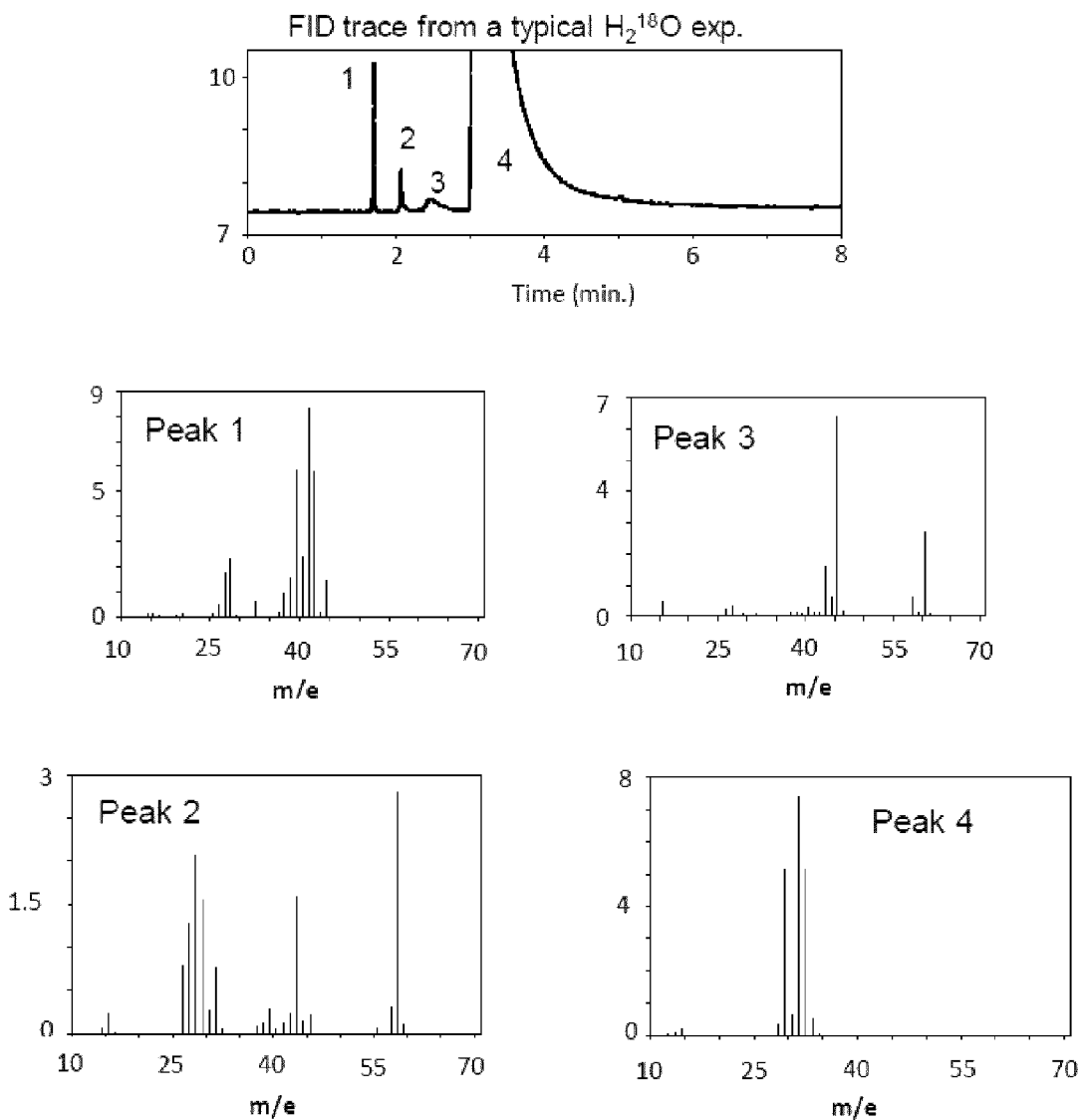
FIG. 6 shows the flame ionization detector (FID) trace from a filtered liquid reaction product at the end of a typical experiment with $^{18}O$ labeled water and methanol (5:95) (Example 2). Reaction conditions: total pressure 480 kPa, temperature 40° C., 40 mL min$^{-1}$ total flowrate, 2.5% CO, 1.25% $O_2$, 1.6% propene, balance He. The MS patterns for the four peaks labeled 1 to 4 are shown below the trace. The pattern for peak 1 matches that of propene (retention time 1.70 min), peak 2 propene oxide-$^{16}O$ (retention time 2.06 min), peak 3 acetone, mostly labeled with $^{18}O$ (retention time 2.39 min), and peak 4 methanol-$^{16}O$ (retention time 3.15 min).
Figure 7:
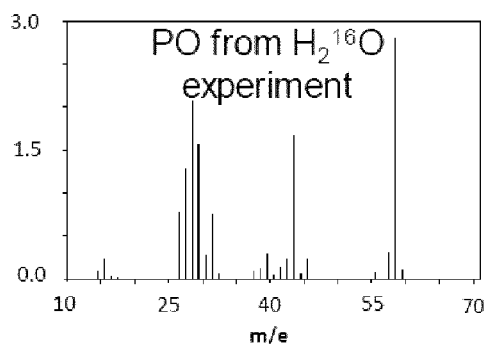
FIG. 7 shows mass spectrometry (MS) patterns of propene oxide from various sources (Example 2). The top two are propene oxide (PO) from experiments using $H_2^{16}O$ (left) and $H_2^{18}O$ (right). Reaction conditions: 95:5 MeOH:$H_2O$, total pressure 480 kPa, temperature 40° C., 40 mL min$^{-1}$ total flowrate, 2.5% CO, 1.25% $O_2$, 1.6% propene, balance He. The one labeled "PO from $H_2^{18}O$ flooding expt" is the cracking pattern of propene oxide from a solution of propene oxide in $^{18}O$ labeled water. "Water peak from $H_2^{18}O$ exp" is the pattern of the water peak eluted from the GC column. The bottom two patterns are PO standards injected as pure compound (left) of a 6 mM solution in methanol.
Figure 7:
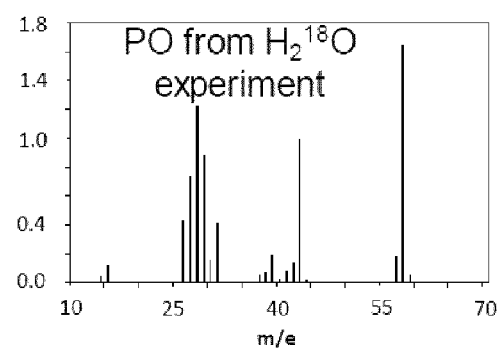
Figure 7:
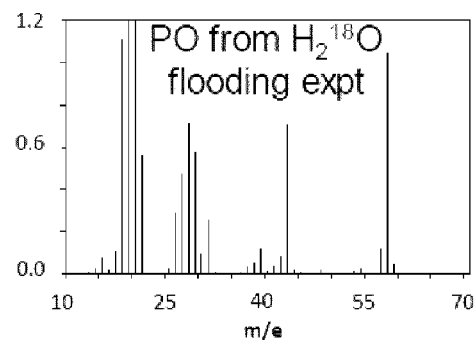
Figure 7:
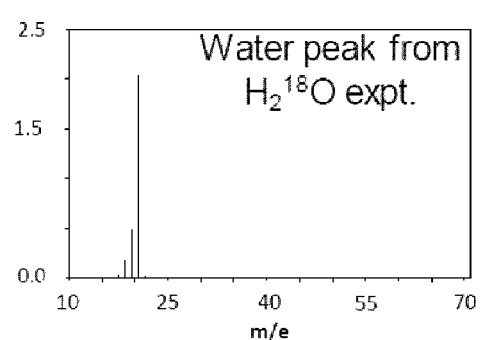
Figure 8:
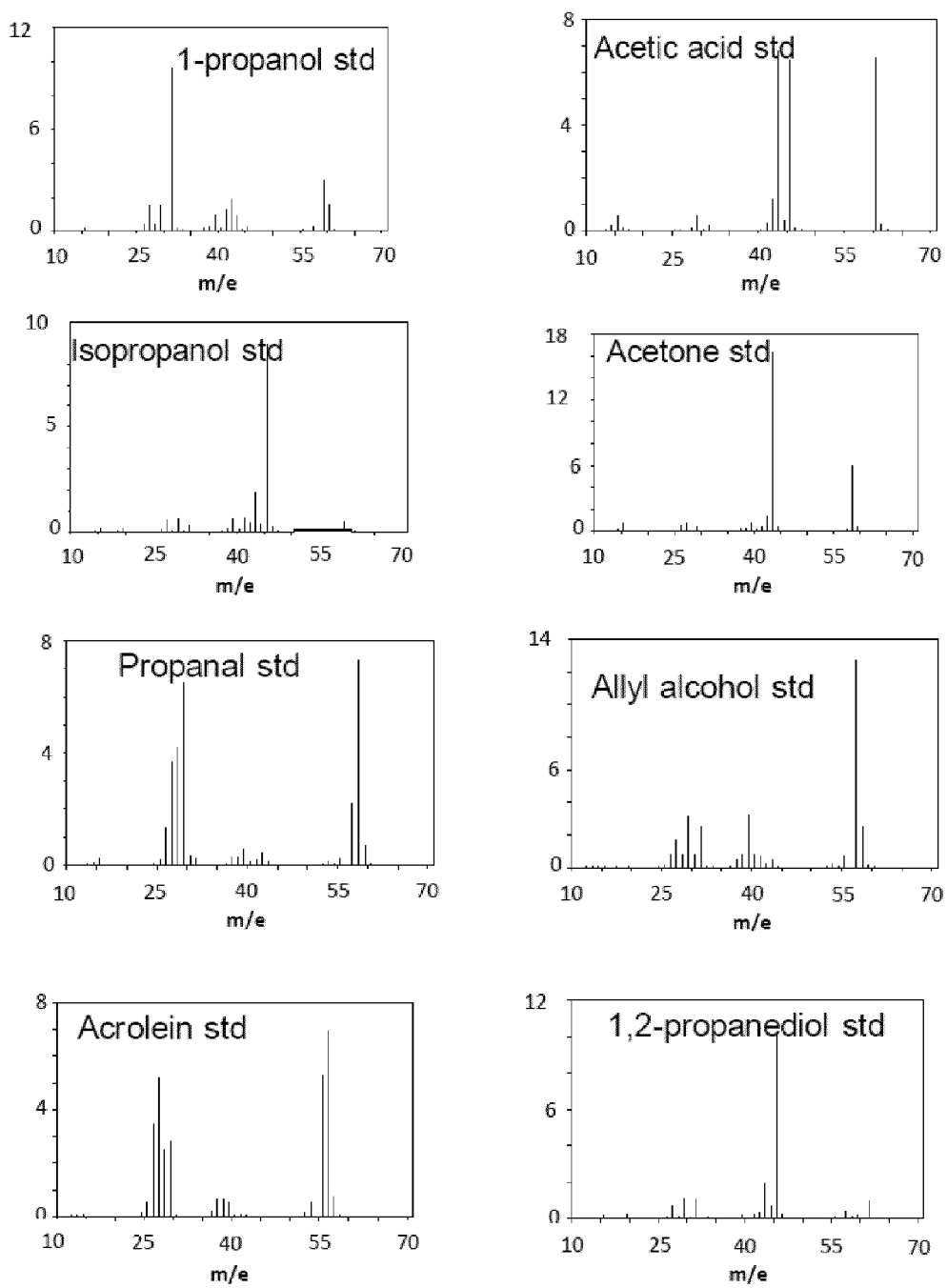
FIG. 8 shows the MS patterns of various standards injected as pure compounds into the GC-MS (Example 2).

Catalytic Tests:

The epoxidation reaction was carried out in a Lab-Crest pressure glass reactor which was filled with 50 mL of solvent. The solvent used was either ion-exchanged distilled water or anhydrous CH$_3$OH, or their mixture. The feed gas, at a flow rate of 40 mL min$^{-1}$, was adjusted to the desired composition using mass flow controllers, and flowed into the liquid through a 5 μm stainless steel porous frit. The pressure in the vessel was maintained at 480 kPa with a back pressure regulator. The temperature of the liquid in the reactor was maintained at 40° C. with the help of an external water bath. Before the experiment began, the catalyst mixture (typically 0.1 g Au/TiO$_2$ and 0.15 g TS-1) was placed in a small polyethylene cup held with a small, Teflon-covered magnet above the liquid. The feed composition was adjusted, the CO oxidation activity of the catalyst was tested, and the system was allowed to reach a steady state. Then, the catalyst cup was guided by a magnet into the liquid that was stirred constantly to commence the experiment. The exit gas was sampled regularly with a gas chromatograph. At the conclusion of the experiment, the liquid was analyzed by gas chromatography and product identification was assisted by GC-MS. Isotopic labeling was determined using a GC-MS. FIGS. 6-8 and Table 2 show the mass spectra of the compounds of interest, results of the isotope labeling experiments, and GC analysis information. The peroxide content was determined by titration with cerium sulfate using a ferroin indicator.

TABLE 2

Retention Times for Species Measured by GC-MS

| Species | Retention Time (min) |
|---|---|
| Propene Oxide | 2.06 |
| Acetone | 2.39 |
| Acetic acid | 7.70 |
| 1-propanol | 4.86 |
| Isopropanol | 3.54 |
| 1,2-propanediol | 8.83 |
| Allyl alcohol | 5.58 |
| Propanal | 2.23 |
| Acrolein | 2.56 |

Analysis of TS-1:

About 0.039 g of the TS-1 was dissolved completely in 2 mL distilled deionized (DDI) water and 3 mL 48% HF. The resulting solution was further diluted with 45 mL water, which was then analyzed using ICS-EAS.

Product Analysis:

The gas phase products were analyzed by on-line gas chromatography (Agilent 6890 GC) using two columns: a carbosphere packed column with a thermal conductivity detector (TCD) for analysis of CO, O$_2$ and CO$_2$, and a Econo-cap EC-Wax capillary column with a FID detector for organics. The liquid product was also analyzed by the same capillary column by injecting a small sample of the liquid with a syringe. All liquid products were separated from the solid catalysts by filtration through a 0.2 μm an PVDF membrane (Pall) before analysis. The isotope distributions were determined using a GC-MS (Agilent 6890 GC with 5973 MSD) with the FID and MSD sharing a capillary column via a splitter.

$H_2O_2$ and/or alkylhydroperoxide were titrated as follows. A ferroin indicator solution was prepared by dissolving 0.123 g iron(II) sulfate heptahydrate ($FeSO_4.7H_2O$) into 15 mL DDI water, then adding 0.259 g 1,10-phenanthroline. The titration solution was prepared by dissolving 0.114 g cerium (IV) sulfate ($Ce(SO_4)_2$) into dilute sulfuric acid (1/19 v/v). Into a conical flask, 5 mL sample and 10 mL diluted sulfuric acid (1/19 v/v) were added. Two drops of ferroin indicator were added to the above solution, turning it red. The titration solution, 0.6875 mM $Ce(SO_4)_2$, was then added until a color change to pale blue was observed.

Reactor System:

The reactor was a Lab-Crest pressure glass reactor (Cole-Parmer) into which a stream of premixed gas flows and is dispersed with a 5 μm stainless steel porous frit (Scientific Instrument Services). The pressure in the reactor was maintained with a back pressure regulator (Mighty Mite). A polyethylene cup was used to hold the catalyst above the liquid by placing a teflon-coated magnetic bar in the basket and holding it in place with another magnet outside the reactor. When the external magnet was removed, the catalyst would drop into the liquid and disperse. The gas composition was adjusted using mass flow controllers (Brooks). The temperature of the reactor was maintained by placing it in a water bath.

Results

The CO oxidation-assisted epoxidation process was conducted by bubbling a gas mixture of CO, $O_2$, propene, and He through a suspension of $Au/TiO_2$ and TS-1 catalysts. In a typical experiment, the feed gas was 2.5% CO, 1.25% $O_2$, and 1.6% propene in He and the total pressure was 480 kPa. The rates of CO, $O_2$, and propene consumption and formation of volatile products, including propene oxide (PO), acetone, propanediol, and 2-propanol were monitored by analyzing the gas phase products at the reactor exit periodically with an on-line GC-MS. $CO_2$ was also analyzed, but its rate of formation could not be calculated accurately from the exit gas due to significant dissolution into the liquid. At the conclusion of the experiment, the liquid phase was analyzed for organic products by GC-MS, and peroxides by titration. The results are presented in Table 3.

TABLE 3

Summary results for liquid phase CO oxidation-assisted epoxidation of propene.

| | Reaction conditions | | Rxn time, min. | Reaction rate,[b] μmol/min | | | Total PO, ±1 | Quantity, $\times 10^{-5}$ moles[c] | | —OOH[g] ±0.2 | PO/CO[d] |
|---|---|---|---|---|---|---|---|---|---|---|---|
| | | | | | | | | Other products[f] | $C_3H_6$ cons. ±2 | | |
| Exp.[a] | MeOH:$H_2O$ | CO, $O_2$, propene[e] | | CO | $O_2$ | $C_3H_6$ | | | | | |
| 1 | 0:50 | 2.5, 1.25, 1.6 | 292 | 2.5 | 1.6 | 0.83 | 2.7 | 14.6 | 24 | 0.34 | 0.04 |
| 2 | 40:10 | 2.5, 1.25, 1.6 | 232 | 11 | 5.8 | 0.88 | 21 | trace | 22 | 0.72 | 0.08 |
| 3 | | 2.5, 1.25, 3.3 | 221 | 9.3 | 5.5 | 0.97 | 28 | trace | 22 | nd | 0.14 |
| 4 | | 1.25, 1.25, 1.6 | 234 | 5.6 | 3.0 | 0.58 | 12 | trace | 12 | nd | 0.1 |
| 5 | 47.5:2.5 | 2.5, 1.25, 1.6 | 251 | 4.0 | 2.5 | 0.81 | 23 | trace | 20 | 0.37 | 0.22 |
| 6 | | 2.5, 1.25, 3.3 | 235 | 5.5 | 3.6 | 1.1 | 27 | trace | >26 | nd | 0.21 |
| 7 | 50:0 | 2.5, 1.25, 1.6 | >100 | 0 | 0 | 0 | 0 | 0 | 0 | nd | — |
| 8 (EtOH) | 47.5[h]:2.5 | 2.5, 1.25, 1.6 | 240 | 1.8 | 1.1 | .08 | 1.5 | trace | 2 | nd | 0.03 |
| 9 ($CH_3CN$) | 47.5[i]:2.5 | 2.5, 1.25, 1.6 | 240 | 0.4 | 0.2 | 0.0 | 0 | 0 | 0 | nd | — |
| 10[j] (control) | 47.5:2.5 | 2.5, 1.25, 1.6 | 185 | 7.2 | 3.8 | 0.002 | 0.2 | trace | 3 | 2.1 | <0.01 |
| 11 (control) | 40:10 | 0, 1.25, 1.6 | 205 | — | 0 | 0 | 0 | 0 | 0 | nd | — |

[a]Catalyst: $Au/TiO_2$ + TS-1, except when noted; 40° C.; total pressure: 480 kPa; total flow rate 40 mL/min; 50 mL liquid. All data shown are averages of two or three separate experiments. Data for each row are average of at least two separate experiments.
[b]Steady state rates, determined by analysis of composition of gas exiting the reactor.
[c]Sum of products formed or reactant consumed over the reaction time indicated, determined from both the gas and liquid phase compositions.
[d]Ratio of total epoxide detected to total CO consumed.
[e]% by volume, balance He.
[f]Only by product detected in any significant amount was propanediol in Exp. 1.
[g]Total peroxide ($H_2O_2$ + ROOH), determined by titration analysis of liquid reaction mixture at conclusion of experiment.
[h]Methanol solvent was replaced with ethanol.
[i]Methanol solvent was replaced with acetonitrile.
[j]Catalyst: $Au/TiO_2$ + silicalite.

When the catalyst was above the liquid, CO was oxidized to $CO_2$ with stoichiometric consumption of $O_2$, independent of the presence of propene in the feed or the liquid composition. There was no detectable reaction of propene when it was present. A similar stoichiometric consumption of CO and $O_2$ was observed when $Au/TiO_2$ was lowered into a water-only solvent in a feed without propene. On the other hand, in a feed that includes propene, extra O consumption ($O_{xs}$), beyond what was required for stoichiometric CO oxidation, was observed immediately when a $Au/TiO_2$+silicalite catalyst mixture was lowered into a 20:80 $H_2O$/methanol solvent. However, the rate of $O_{xs}$ consumption fell quickly to an undetectable level within an hour. At the conclusion of the experiment, about 21 μmole of peroxide were detected in the aqueous solution (Exp. 10 in Table 3). Silicalite, which has the same crystal structure as TS-1 but without Ti incorporation, is inactive for epoxidation. The quantity of peroxide detected was about ¼ that of $O_{xs}$. The fate of the remaining $O_{xs}$ was not determined.

Figure 9:
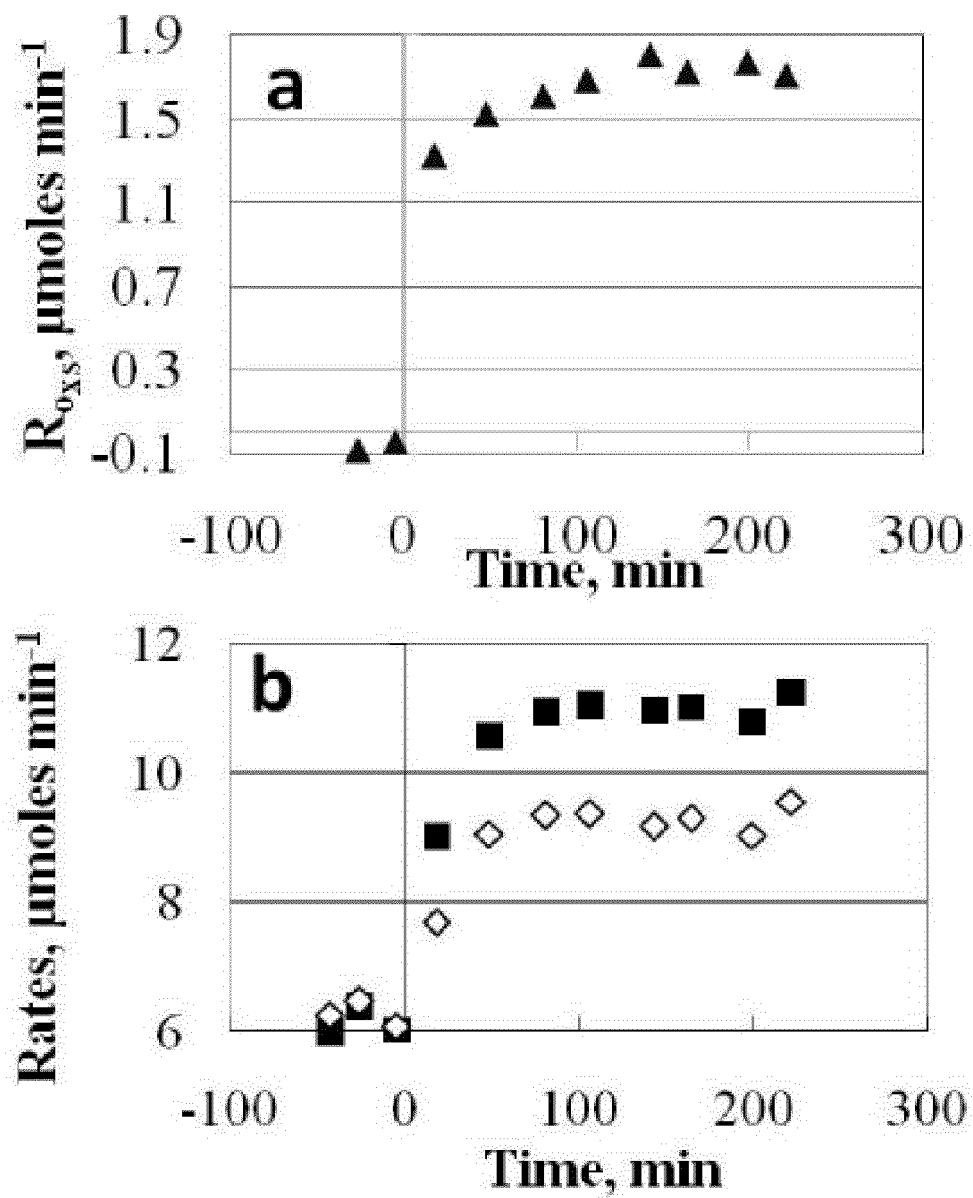
FIG. 9 shows the rates of (a) extra O consumption, $R_{Oxs}$, and (b) O atom (=$2 \times O_2$, ■) and CO (◇) consumption (Example 2). Catalyst: $Au/TiO_2$+TS-1, 2.5% CO, 1.25% $O_2$ and 6.6% $C_3H_6$, balance He, 40° C. At time zero, the catalyst mixture was lowered into the solvent ($CH_3OH:H_2O=80:20$).

With propene in the feed and a mixture of $Au/TiO_2$ and TS-1 as catalyst in a methanol-$H_2O$ solvent, the rate of $O_{xs}$ consumption was maintained over the course of the experiment (FIG. 9a). The CO and $O_2$ consumption rates reached a steady state in ~1 h (FIG. 9b), whereas propene consumption rate required ~2 h, probably due to its higher solubility in the solvent. Over this time, epoxide began to appear in the gas phase. Its concentration increased continuously, consistent with the fact that it was accumulating in the liquid. At the completion of the experiment, the liquid was analyzed for the propene oxide contents. As illustrated by experiments 1 to 7 in Table 3, the product distributions and the reaction rates depended strongly on the solvent. In pure $H_2O$ (Exp. 1), the catalyst was active, but the major product was propanediol, indicating rapid hydrolysis of propene oxide. At the other extreme when anhydrous methanol was the solvent, there was little reaction, even for CO oxidation (Exp. 7). Very interestingly, propene oxide was practically the only product of propene reaction in experiments when the solvent was methanol with 5 or 20% $H_2O$ (Exp. 2 to 6). This could be a consequence of the hydrophobic nature of the TS-1 pores that partitions $CH_3OH$ preferentially to $H_2O$. Within the uncertainties (estimated 10%) in both $O_2$ and propene balances over the course of the experiment, little combustion or hydration of propene had occurred under these conditions. Titration identified the presence of peroxide in the liquid ($2^{nd}$ to last column, Table 3), but the technique could not distinguish $H_2O_2$ from other peroxides, such as $CH_3OOH$. The yield of propene oxide increased with CO reaction rate, which increased with CO concentration in the feed (compare Exp. 2 and 4). The yield also increased with increasing propene concentration (compare Exp. 2 and 3, and 5 and 6).

When methanol was replaced by ethanol (Exp. 8), the CO oxidation rate decreased by a factor of about 2.5, and propene oxide formation by over a factor of 10. The slower epoxidation rate in ethanol than in methanol has been reported, although the decrease was less than that observed here. (See S. M. Danov, A. V. Sulimov and A. V. Sulimova, *Russian Journal of Applied Chemistry*, 2008, 81, 1963-1966.) Importantly, selective propene oxide formation was possible.

Control experiments showed little propene oxide formation when either Au/$TiO_2$ (not shown) or TS-1 (Exp. 10, Table 3) was missing from the catalyst mixture, supporting the hypothesis that a stable intermediate oxidant was formed on Au/$TiO_2$ that diffuses to TS-1 to effect epoxidation. CO was necessary (Exp. 11, Table 3), confirming that this intermediate oxidant cannot be formed by oxidation of water or methanol directly, but by a mechanism that is coupled to CO oxidation. Finally, when methanol was replaced by acetonitrile in the solvent (95/5 acetonitrile/$H_2O$, Exp. 9), no propene oxide was formed, no peroxide was detected in the liquid by titration, and the CO oxidation activity was low.

The lack of catalytic activity in an anhydrous methanol solvent is not surprising. Others have reported the importance of moisture for high CO oxidation activities. (See Costello, C. K. et al., *Applied Catalysis, A: General* 243 (1), 15 (2003); Daté, M., Okumura, M., Tsubota, S., and Haruta, M., *Angewandte Chemie International Edition* 43 (16), 2129 (2004); and Kung, M. C., Davis, R. J., and Kung, H. H., *Journal of Physical Chemistry C* 111 (32), 11767 (2007)). Surprising results were obtained, however, when the role of $H_2O_2$ was investigated in the epoxidation reaction using $H_2{}^{18}O$ in a methanol-$H_2O$ solvent. If epoxidation proceeded via the formation of $H_2O_2$ from $H_2O$ and $O_2$, $H_2{}^{18}O$ could be used to form $H^{18}O^{16}OH$, and the resulting propene oxide would be 50% labeled as $C_3H_6{}^{18}O$. Table 4 shows the results of these experiments (Exps. 12-14). Only $^{16}O$-labeled PO was detected both in the exit gas and the liquid. In contrast, a distribution of $C^{16}O_2$, $C^{16}O^{18}O$, and $C^{18}O_2$, enriched in $^{18}O$ content, was detected in the gas phase product. The formation of a distribution of isotopically labeled $CO_2$ indicates oxygen scrambling between $CO_2$ and $H_2O$, most likely via a bicarbonate intermediate.

TABLE 4

Results of $^{18}O$-Labeled Experiments

| Exp.[a] | $H_2O$ isotope ratio, $^{18}O/^{16}O$ | $O_2$ isotope ratio, $^{18}O/^{16}O$ | Reaction time, min | $C^{18}O_2:C^{18}O^{16}O:C^{16}O_2$ | $P^{18}O:P^{16}O$ |
|---|---|---|---|---|---|
| 12 | 1/0 | 0/1 | 310 | 4.8:6.8:1 | 0:1 |
| 13 | 1/0 | 0/1 | 110 | 5.2:6..4:1 | 0:1 |
| 14 | 1/0 | 0/1 | 120 | 4.8:6.3:1 | 0:1 |
|    |     |     | 240 | 4.8:6.3:1 | 0:1 |
| 15 | 0/1 | 1/0 | 60  | 0:0.1:1 | 1:0 |
|    |     |     | 180 | 0:0.1:1 | 1:0 |
| 16 | 0/1 | 1/0 | 120 | 0:0.02:1 | 1:0 |
| 17 | 0/1 | 1/0 | 120 | 0:0.1:1 | 1:0 |
|    |     |     | 180 | 0:0.1:1 | 1:0 |

[a]Reaction conditions same as Table 3; $CH_3OH/H_2O = 95:5$ except Exp. 16, which was 80:20, and Exp. 17 which used ethanol instead of methanol.
[b]$CO_2$ in the gas product stream, and propene oxide in both gas and liquid products.

Complementary experiments were conducted using $^{18}O_2$ in the feed. The results (Exp. 15 and 16) showed that only $^{18}O$-labeled PO was formed until at least 1 h into the experiment, when small amounts of $^{16}O$-labeled PO began to appear. Interestingly, the $CO_2$ was mostly labeled with $^{16}O$, consistent with rapid isotope scrambling with water. A similar observation was obtained using the ethanol/$H_2O$ solvent (Exp. 17). Only $^{18}O$-labelled PO was formed when using $^{18}O_2$. In addition to the fact that the methanol results have been repeated, other evidence also suggested that these results were not experimental artifacts due to scrambling in the detection system. Injection of a solution of unlabelled propene oxide in $H_2{}^{18}O$ into the GC-MS did not change the cracking pattern of the propene oxide, although a huge m/e=20 peak due to the labelled water was observed. In the experiments using $H_2{}^{18}O$, trace amounts of $^{18}O$-labelled (>90% labelled) acetone could be detected, which was likely formed by hydration of propene followed by oxidative dehydrogenation of the propanol product. Thus, labelled reactive organics can be detected accurately.

These results show that $H_2O$, although necessary for CO oxidation, is not involved directly in the epoxidation reaction. It is believed that the role of moisture is to maintain the activity of the active site on Au for CO oxidation. Alcohol is needed for epoxidation, which does not occur in the acetonitrile/water solvent. Whereas the data unequivocally showed the formation of a stable intermediate oxygen carrier that is formed from $O_2$ on Au/$TiO_2$, and diffuses to TS-1 to effect epoxidation, unfortunately, there was no direct observation on the nature of this intermediate. Two logical possibilities are: $H_2O_2$ and $CH_3OOH$ (or $C_2H_5OOH$ if ethanol is used).

Figure 10:
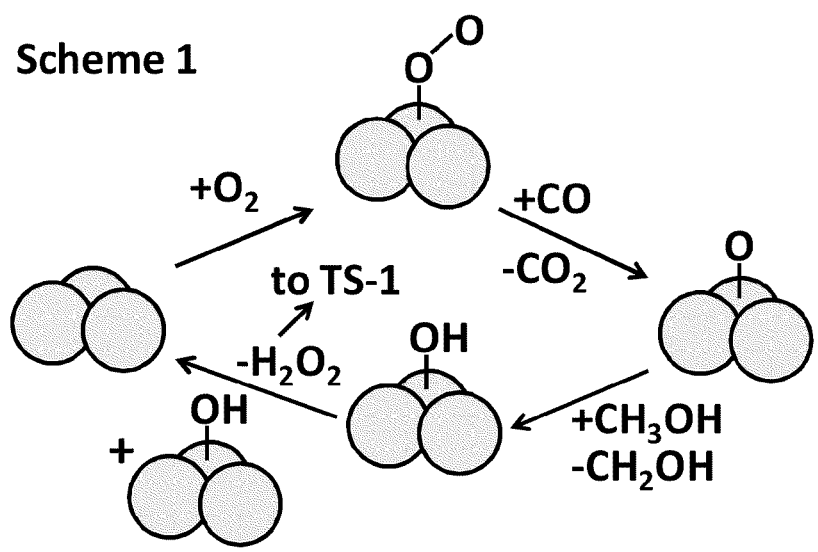
FIG. 10 shows Schemes 1 and 2: Proposed mechanisms for formation of oxygen-carrying intermediate (Example 2).
Figure 10:
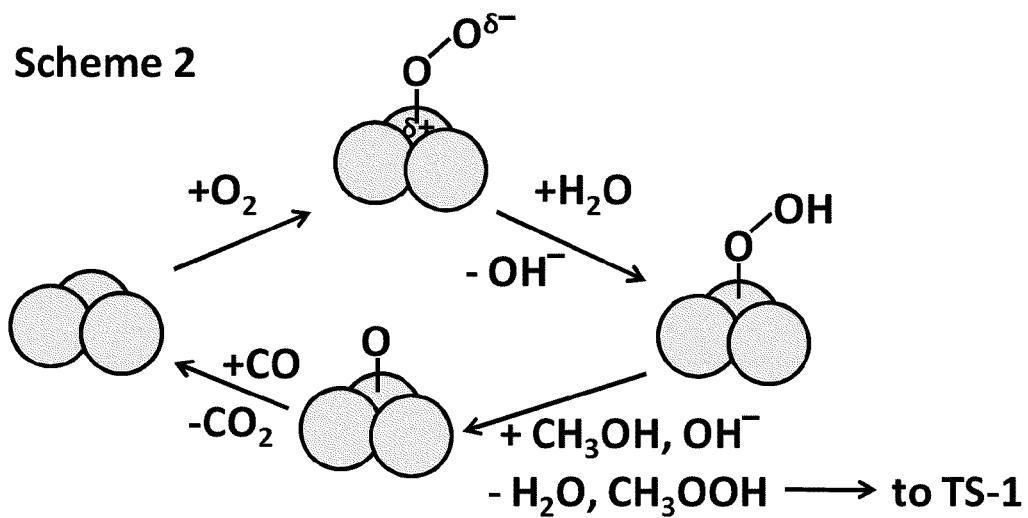

$H_2O_2$ could be formed according to Scheme 1 shown in FIG. 10. $O_2$ is adsorbed on the active site on Au/$TiO_2$ as peroxy or superoxide, which reacts with CO to form $CO_2$ and an adsorbed O. The adsorbed O may react with another CO in a nonproductive pathway, or react with methanol to form a surface OH and a $CH_2OH$ radical. Two surface OH combine to form $H_2O_2$ which carries the same isotope label as $O_2$. This mechanism would postulate $HOCH_2CH_2OH$ as a byproduct. Unfortunately, its presence was not detected, although its concentration might be too low for detection.

Alternatively, the Au-superoxide picks up a proton from water or methanol to form Au-peroxide (Scheme 2 in FIG. 10), which reacts with methanol or methoxide to form $CH_3OOH$, in which the O of the OH would have the same isotope label as $O_2$. The methylhydroperoxide is responsible for propene epoxidation. Reaction of Au-superoxide with CO would lead to nonproductive consumption of CO.

As used herein, and unless otherwise specified, "a" or "an" means "one or more." All patents, applications, references, and publications cited herein are incorporated by reference in their entirety to the same extent as if they were individually incorporated by reference.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like includes the number recited and refers to ranges which can be subsequently broken down into subranges as discussed above. Finally, as will be understood by one skilled in the art, a range includes each individual member.

It is specifically intended that the present invention not be limited to the embodiments and illustrations contained herein, but include modified forms of those embodiments including portions of the embodiments and combinations of elements of different embodiments as come within the scope of the following claims.

We claim:

1. A method for the epoxidation of an alkene, the method comprising exposing the alkene to a two-component catalyst system in an aqueous solution, in the presence of carbon monoxide and molecular oxygen, under conditions in which the alkene is epoxidized, wherein the two-component catalyst system comprises a first catalyst that generates peroxides or peroxy intermediates during oxidation of CO with molecular oxygen and a second catalyst catalyzes the epoxidation of the alkene using the peroxides or peroxy intermediates.

2. The method of claim 1, wherein the first catalyst comprises gold and the second catalyst comprise titanium silicalite.

3. The method of claim 1, wherein the alkene has an allylic hydrogen.

4. The method of claim 3, wherein the alkene is butene.

5. The method of claim 3, wherein the alkene is propene.

6. The method of claim 1, wherein the aqueous solution comprises an alcohol.

7. The method of claim 6, wherein the alcohol is methanol.

8. The method of claim 7, wherein the alkene has an allylic hydrogen.

9. The method of claim 6, wherein the ratio of alcohol to water in the aqueous solution is at least 4:1 by volume.

10. The method of claim 6 having a selectivity for epoxide production of at least 90%.

11. The method of claim 10 having a selectivity for epoxide production of at least 99%.

12. The method of claim 1, wherein the epoxidation of the alkene is carried out at a temperature of no greater than 50° C.

13. The method of claim 1 carried out in the absence of $H_2$ gas.

14. The method of claim 1 carried out in the absence of peroxy initiators.

15. The method of claim 1 carried out in the absence of $H_2$ or peroxy initiators, wherein the first catalyst comprises gold and the second catalyst comprises titanium silicalite, the alkene has an allylic hydrogen, and the aqueous solution comprises methanol.

* * * * *